(12) United States Patent
Gehman et al.

(10) Patent No.: US 8,560,040 B2
(45) Date of Patent: Oct. 15, 2013

(54) SHIELDED BIOMEDICAL ELECTRODE PATCH

(71) Applicants: Stacy Gehman, Bothell, WA (US); Earl Herleikson, Bothell, WA (US); Steven Hugh, Bothell, WA (US); Thomas Lyster, Bothell, WA (US); Thomas Solosko, Bothell, WA (US)

(72) Inventors: Stacy Gehman, Bothell, WA (US); Earl Herleikson, Bothell, WA (US); Steven Hugh, Bothell, WA (US); Thomas Lyster, Bothell, WA (US); Thomas Solosko, Bothell, WA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/668,681

(22) Filed: Nov. 5, 2012

(65) Prior Publication Data

US 2013/0060115 A1    Mar. 7, 2013

Related U.S. Application Data

(62) Division of application No. 12/667,597, filed on Jan. 4, 2010, now abandoned.

(51) Int. Cl.
*A61B 5/04* (2006.01)
*A61B 5/0408* (2006.01)
*A61B 5/0416* (2006.01)
*A61B 5/0424* (2006.01)

(52) U.S. Cl.
USPC ........... 600/372; 600/391; 600/392; 600/393; 600/394

(58) Field of Classification Search
USPC .......................................... 600/372, 391–394
See application file for complete search history.

(56) References Cited

U.S. PATENT DOCUMENTS

| | | | | | |
|---|---|---|---|---|---|
| 4,029,086 | A | * | 6/1977 | Corasanti | 600/391 |
| 4,257,424 | A | * | 3/1981 | Cartmell | 600/391 |
| 4,442,315 | A | * | 4/1984 | Segawa | 174/36 |
| 4,763,660 | A | * | 8/1988 | Kroll et al. | 600/391 |
| 5,626,135 | A | * | 5/1997 | Sanfilippo | 600/391 |
| 7,512,449 | B2 | * | 3/2009 | Lang et al. | 607/152 |
| 7,532,921 | B2 | * | 5/2009 | Eichler | 600/372 |
| 2007/0043284 | A1 | * | 2/2007 | Sanfilippo | 600/391 |

FOREIGN PATENT DOCUMENTS

| | | | |
|---|---|---|---|
| EP | 1752093 | A | 2/2007 |
| GB | 2185403 | A | 7/1987 |
| WO | 99/56619 | A | 11/1999 |
| WO | 03/047427 | A | 6/2003 |
| WO | 2007/060609 | A | 5/2007 |
| WO | 2007/063436 | A | 6/2007 |

* cited by examiner

*Primary Examiner* — Lee S Cohen (57) ABSTRACT

A biomedical electrode patch having improved resistance to capacitive coupling to extraneous electric fields. The patch includes a conductive shield and a contact portion formed on an upper surface thereof. The contact portion extends through the film layer and contacts an electrode formed of a material suitable for conducting electrical signals from a patient. Conductive traces formed on the lower surface of the tab extend to contact pads. A nonconductive layer is printed over the traces and can have a shield formed thereon.

7 Claims, 10 Drawing Sheets

SHIELDED BIOMEDICAL ELECTRODE PATCH

This Application is a divisional of U.S. Ser. No. 12/667,597, now abandoned, which is the National Stage of International Application No. PCT/IB2008/052645 filed on Jul. 1, 2008, and which further claims priority to U.S. Provisional Application No. 60/948,355 filed on Jul. 6, 2007, each of which is incorporated herein by reference in its entirety.

This invention relates to electrode patches for placement on a patient's body to measure physiological signals.

In many biomedical applications, electronics and therapy devices need to be attached to the skin in order to observe and administer therapy or to monitor patient conditions such as blood flow, heart rhythm, and blood oxygen levels. Some common devices include electrodes for generating an electrocardiograph, external defibrillators, pacing devices, transcutaneous nerve stimulation devices, and transdermal drug delivery systems. Often these devices will remain attached to the skin for an extended period of time.

Conductive components in existing electrodes are exposed to electric fields from a number of sources. The modern home and hospital room have many electronic devices and associated cables that may interfere with operation of an electrode. This is particularly true for ambulatory patients. Electrodes affixed to ambulatory patients are particularly susceptible to electric fields caused by clothing-generated static. Because of its inherent capacitance the electrode will generate current in response to these electric fields that will interfere with the accuracy of signals sent from and received by the electrode.

The problem of external electric fields is particularly pronounced where a patient is ambulatory. Electrodes worn by a patient beneath clothing are susceptible to noise created by clothing-generated static, which creates very large amplitude noise that may interfere with or completely obscure the biomedical signal being monitored.

In view of the foregoing it would be advantageous to provide an electrode that is suitable for attaching to a patient's skin and is shielded from ambient electric fields.

One aspect of the invention includes a biomedical electrode patch including a film layer having a conductive shield and a contact portion printed on the upper surface. The shield and contact portion are isolated from one another on the upper surface. The contact portion extends through the film layer and contacts an electrode formed of a material suitable for conducting electrical signals from a patient's skin.

In another aspect of the invention the film layer includes an electrode portion and an elongated tab portion extending from the electrode portion. Contact portions are printed on the lower surface of the electrode portion. Traces printed on the lower surface of the trace portion extend onto the electrode portion and connect with the contact pads. A shield layer is printed on the upper surface of the electrode and trace portions of the film layer.

In another aspect of the invention, a ground trace is formed on the lower surface of the trace portion and is coupled through the film layer to the shield layer. A trace shield layer is printed on the lower surface of the trace portion over the traces. A non-conductive layer separates the trace shield layer from the traces, except for the ground trace that is electrically coupled to the trace shield layer.

In another aspect of the invention, a receptacle secures to the shield layer and includes a shield contact and a contact portion contact. A plug having contacts corresponding to the shield contact and contact portion contact is positionable within the receiver.

Figure 1:
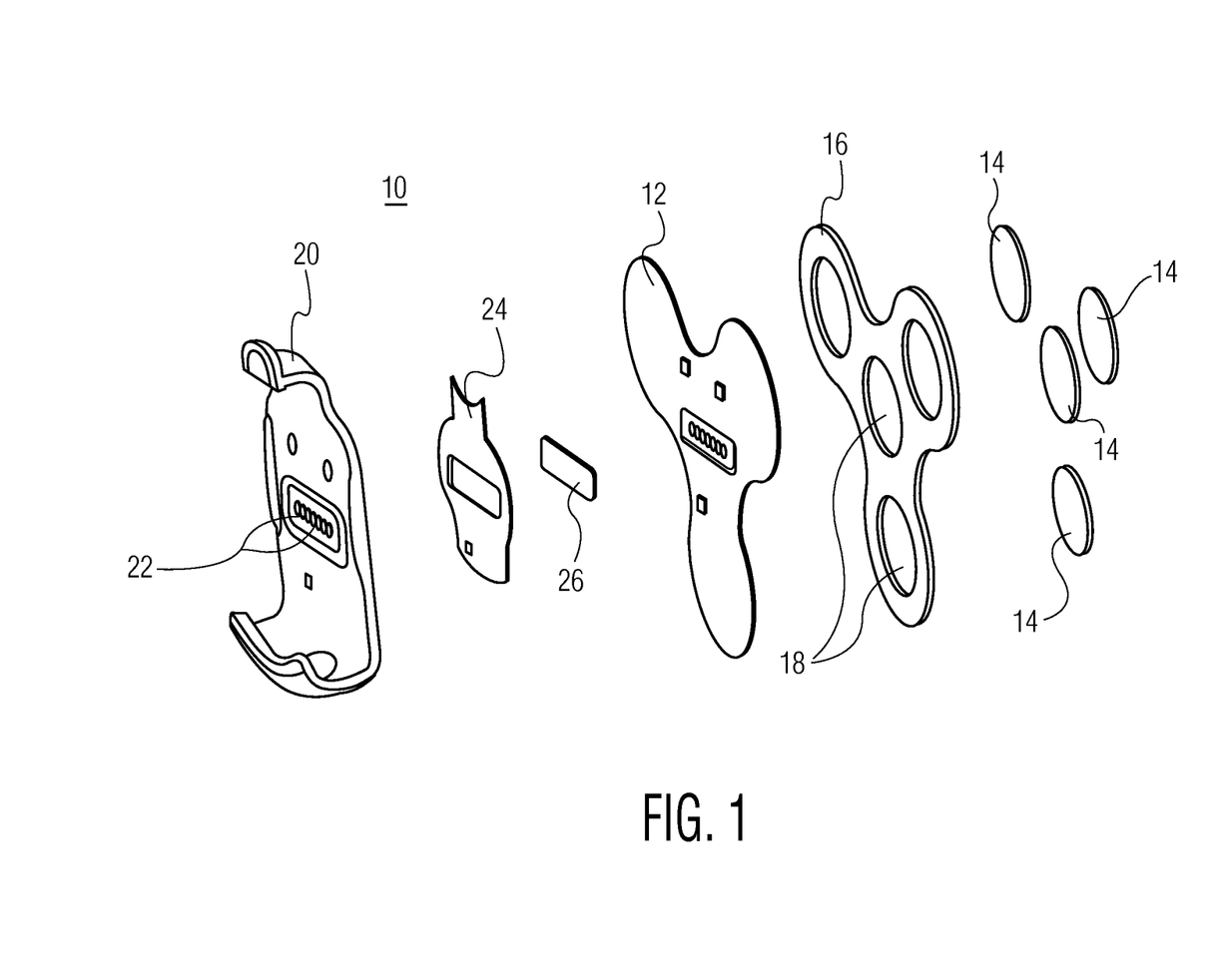
FIG. 1 is an exploded view of a biomedical patch in accordance with an embodiment of the present invention.

Referring to FIG. 1, a biomedical electrode patch 10 includes a conductive layer 12 electrically coupled to one or more electrodes 14 formed of a material suitable for conducting electrical signals to and from a patient's skin. In a preferred embodiment the electrodes 14 are formed of hydrogel, such as Axelgaard's Ag602. The electrode 14 may be formed in sheets and cut to shape or cured in place by means of UV curing or a like process. The patch 10 may include a foam layer 16 having apertures 18 sized to receive the electrodes 14. A surface of the foam layer 16 adjacent a conductive layer 12 may bear an adhesive such as MacTac MP597 serving to secure the foam layer 16 to the conductive layer 12. The foam layer 16 is typically somewhat compressible and can have a thickness slightly less than that of the electrodes 14 such that the electrodes project slightly from the apertures 18. A holster 20 having a plurality of electrical contacts 22 mounts to the conductive layer opposite the electrodes 14. The contacts 22 provide an electrical connection that conducts signals between the patch and a monitoring device or other device (not shown).

The holster 20 is secured to the conductive layer 12 by means of a layer 24 of adhesive, such as a pressure sensitive adhesive (PSA). A layer 26 of conductive PSA may be used to conduct signals from the contacts 22 to the conductive layer 12.

Figure 2:
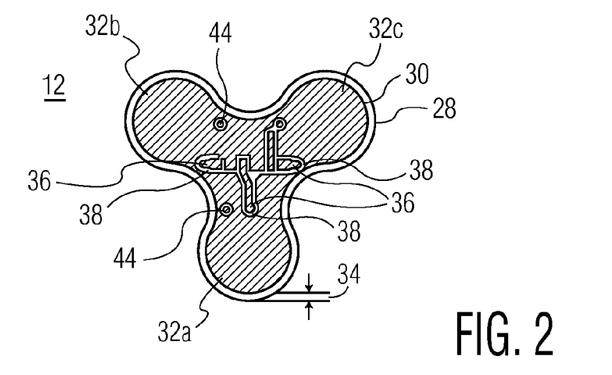
FIG. 2 is a top plan view of a conductive layer bearing a shield layer in accordance with an embodiment of the present invention.

FIG. 2 illustrates an upper surface of the conductive layer 12. The conductive layer 12 in some embodiments may include a film layer 28 made of a non-conductive material, for example, polyester, or a like material. A shield 30 is formed on the conductive layer 12 and may include portions 32a-32c extending over positions corresponding to the electrodes 14. In some embodiments, a dielectric layer is interposed between the shield 30 and the film layer 28. In some embodiments, the shield 30 extends to within a distance 34 from the edge of the film layer 28. In some embodiments, the distance 34 is about 0.025 inches. Providing a non-conductive area around the perimeter of the film layer 28 may reduce the likelihood of undesirable electrical contact between the shield 30 and a patient's skin which is best avoided at times such as when the patient's skin is wet.

In a preferred embodiment, the shield 30 is formed of conductive ink printed on the upper surface of the film layer 28. Suitable inks include silver inks and silver/silver chloride inks, though other conductive inks may be used. The ink may be applied to the film layer 28 by any method known in the art.

A number of contact pads 36 are also formed on a first surface of the film layer 28. The contact pads 36 of the illustrated embodiment are aligned in a row, however other arrangements are possible. The contact pads 36 are preferably arranged in correspondence with conductive members of a device coupling to the patch 10. In the illustrated embodiment, the contact pads 36 are positioned corresponding to the contacts 22 mounted to the holster 20.

A non-conductive gap is formed between the shield 30 and the contact pads 36. However, in some embodiments, a number of the contact pads 36 are separated from the shield 30 and each other by a nonconductive gap whereas one or more of the contact pads 36 is electrically coupled to the shield 30 in order to provide a connection between the shield 30 and, for example, the ground of a monitoring device in order to reduce common mode defects in signals output from the patch 10. In some embodiments, the shield 30 does not extend over the contact pads 36. In such embodiments, the connector or device positioned over the contact pads may provide electrical shielding for the contact pads 36.

Figure 3:
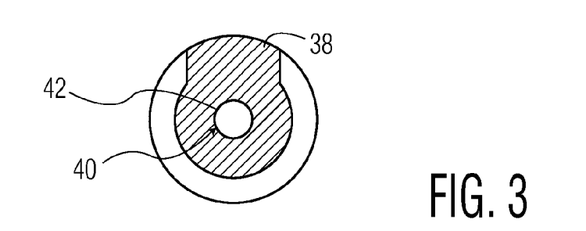
FIG. 3 is a top plan view of a via formed in the conductive layer in accordance with an embodiment of the present invention.

Referring to FIG. 3 while still referring to FIG. 2, traces 38 may connect a number of the contact pads 36 to vias 40 providing a conductive path from a first side of the film layer 28 to a second side opposite the first side. The contact pads 36, traces 38, and vias 40 may be formed of conductive ink, such as silver ink, silver/silver chloride ink, or the like applied by any means known in the art. In the illustrated embodiment, the vias 40 are embodied as holes 42 extending through the film layer and having conductive ink printed on both sides of the film layer 28 around and through the through-holes 42 such that the ink on one side of the film layer is in contact with ink on the other to form an electrical connection.

In some embodiments, alignment marks 44 are printed on the film 28. The alignment marks 44 may be embodied as discrete areas of conductive ink separated from the shield 30 by unprinted areas encircling the alignment marks 44.

Figure 4:
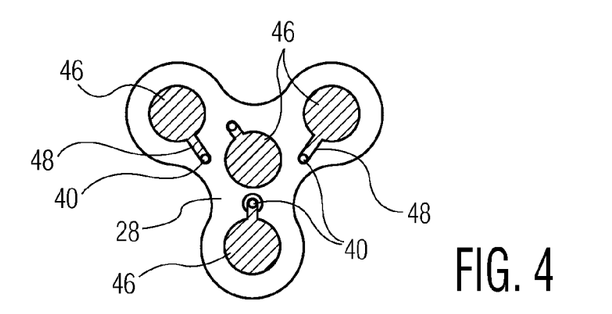
FIG. 4 is a bottom plan view of the conductive layer bearing contact portions in accordance with an embodiment of the present invention.

Referring to FIG. 4, a number of pads 46 are formed on the lower surface of the film layer 28. The pads 46 are typically positioned in correspondence with the electrodes 14 and may have approximately the same area as the electrodes 14. Traces 48 are also formed on the lower surface of the film layer 28, with each trace 48 extending from a via 40 to one of the pads 46. In an alternative embodiment, the vias 40 are co-located with the pads 46 such that traces 48 are unnecessary.

Figure 5:
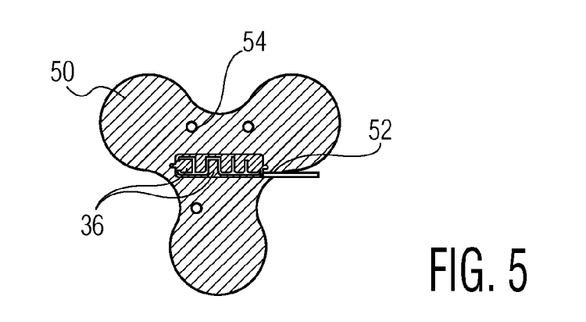
FIG. 5 is a top plan view of the conductive layer bearing a dielectric layer in accordance with an embodiment of the present invention.

Referring to FIG. 5, in some embodiments, a dielectric layer 50 is formed over the shield 30 in order to reduce artifacts caused by finger touches and other electrical contact with the shield 30. The dielectric layer 50 may define an opening 52 over the pads 36 such that the pads 36 are exposed. The dielectric layer 50 may also define openings 54 over the alignment marks 44 such that they remain visible.

Figure 6:
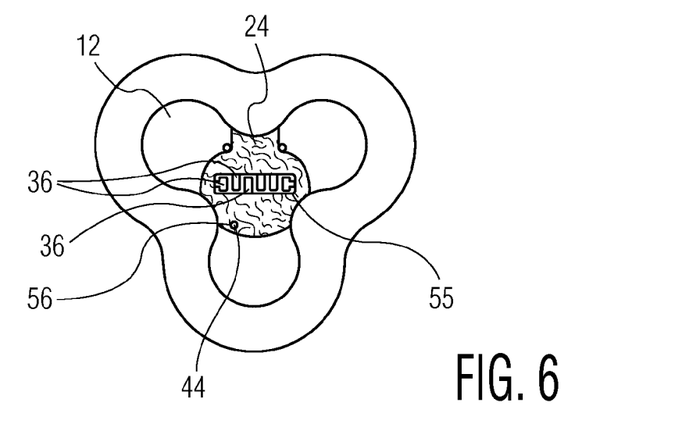
FIG. 6 is a top plan view of the conductive layer bearing an adhesive layer in accordance with an embodiment of the present invention.
Figure 7:
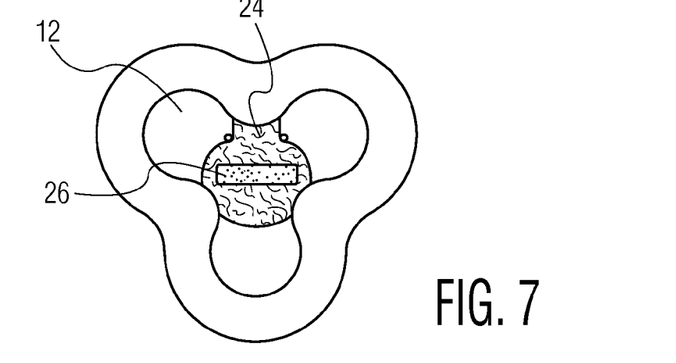
FIG. 7 is a top plane view of the conductive layer bearing a non-isotropically conductive layer in accordance with an embodiment of the present invention.

Referring to FIG. 6, the adhesive layer 24 is secured over the shield layer 30, or the dielectric layer 50 of the conductive layer 12. The adhesive layer 24 may define one or more apertures 55 exposing the contact pads 36. Various types of adhesive may be used to form the adhesive layer 24. In one embodiment 3M's 1524 medical grade PSA is used. The adhesive layer 24 may further define openings 56 exposing the alignment marks 44. Referring to FIG. 7, in some embodiments, a non-isotropically conductive adhesive layer 26 is positioned within the opening 55. The non-isotropic adhesive layer 26 may be formed of a pressure-sensitive adhesive that conducts electricity through the thickness of the layer 26 but does not substantially conduct electricity parallel to the layer 26. In some embodiments, the adhesive layer 24 is eliminated and the layer 26 is enlarged beyond the area of the contact pads to provide sufficient adhesive contact.

Figure 8:
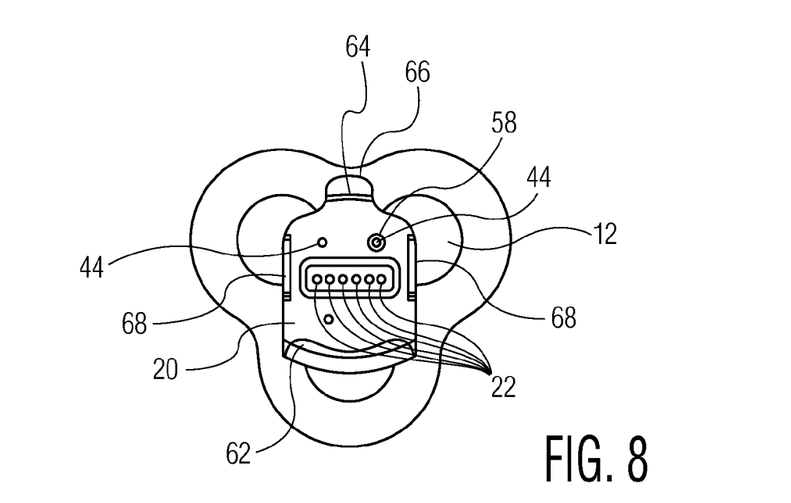
FIG. 8 is a top plan view of a conductive layer having a holster secured thereto in accordance with an embodiment of the present invention.

Referring to FIG. 8, a holster 20 is adhered to the adhesive layer 24 and conductive layer 26. The holster 20 may include openings 58 arranged in a pattern corresponding to one or more of the alignment marks 44. When securing the holster 20 to the adhesive layer a manufacturer may align the openings 58 with the alignment marks 44 to position the holster 20 such that the contacts 22 are aligned with the pads 36. The holster 20 may include a panel (not shown) mounting the contacts 22. In one embodiment, the panel 60 is formed of silicone, or other resilient polymer. One or more locking tabs 62, 64 may be formed on the holster 20 to retain a monitoring device or other connector within the holster. A release tab 66 may be secured to the tab 64 to enable a user to bend the tab 64 out of the way to remove a plug or other connector. Ridges 68 extending along the sides of the holster 20 may serve to align a plug, or other connector, within the holster 20 and hinder lateral movement in order to maintain the monitoring device or other connector aligned with the contacts 22.

Figure 9:
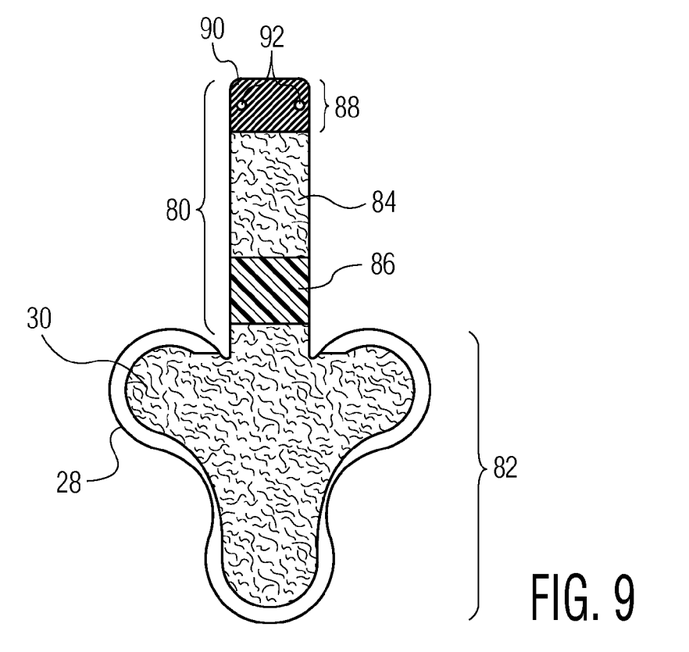
FIG. 9 is a top plan view of an alternative embodiment of a shielded circuit layer for an electrode patch in accordance with an embodiment of the present invention.

Referring to FIG. 9, in an alternative embodiment of an electrode patch 10, a film layer 28 includes a tab portion 80 and an electrode portion 82. In some embodiments, the shield 30 includes a shield tab portion 84 formed over the tab 80. The shield tab portion 84 may be electrically coupled to the shield 30. A dielectric layer may be formed between the film layer 28 and shield 30, including the shield tab portion 84. A transfer adhesive layer 86 may secure to the shield tab portion 82 or electrode portion 80 such that the tab portion 80 may be folded over and secured to the electrode portion 82. The transfer adhesive layer 86 is typically a double sided adhesive film and may include a pressure sensitive adhesive.

A terminal portion 88 of the tab portion 80 may include a stiffener 90 to facilitate coupling of the terminal portion 88 to the holster 20. The stiffener 90 may include one or more alignment holes 92 to facilitate positioning of the terminal portion 88 within the holster 20. The alignment holes may also extend through the film layer 28.

Figure 10:
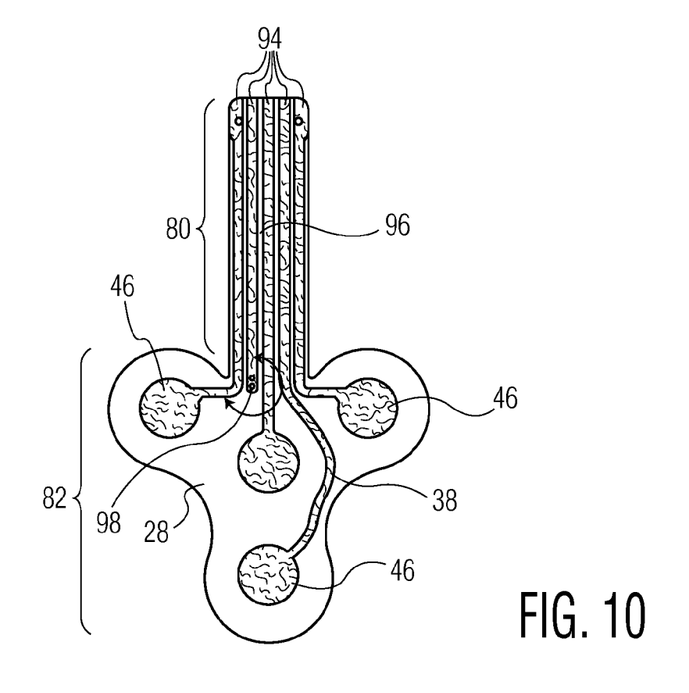
FIG. 10 is a bottom plan view of the shielded circuit layer for the electrode patch of FIG. 9 in accordance with an embodiment of the present invention.

Referring to FIG. 10, the lower surface of the tab portion 80 may include trace tab portions 94 extending from the traces 38 coupled to the pads 46. In some embodiments, a ground trace 96 is also formed on the lower surface of the tab portion 80. One or more vias 98 may extend between the ground trace 96 and the shield tab portion 84. In the illustrated embodiment, the vias 98 are embodied as holes formed in the film layer having conductive ink printed thereon such that conductive ink printed over the upper surface of the film layer contacts ink printed over the lower surface of the film layer 28. Other techniques for conductively connecting the ground trace 96 to the shield tab portion 84 or the shield 30 can be used as well.

In some embodiments a dielectric layer may be printed over the trace tab portions 94 and the ground trace 96. In other embodiments, a lower shield layer may be formed over the dielectric layer. The lower shield layer can be coupled to the shield layer 30 by the ground trace 96 and vias 98. In some embodiments, an additional dielectric layer is formed over the lower shield layer.

Figure 11:
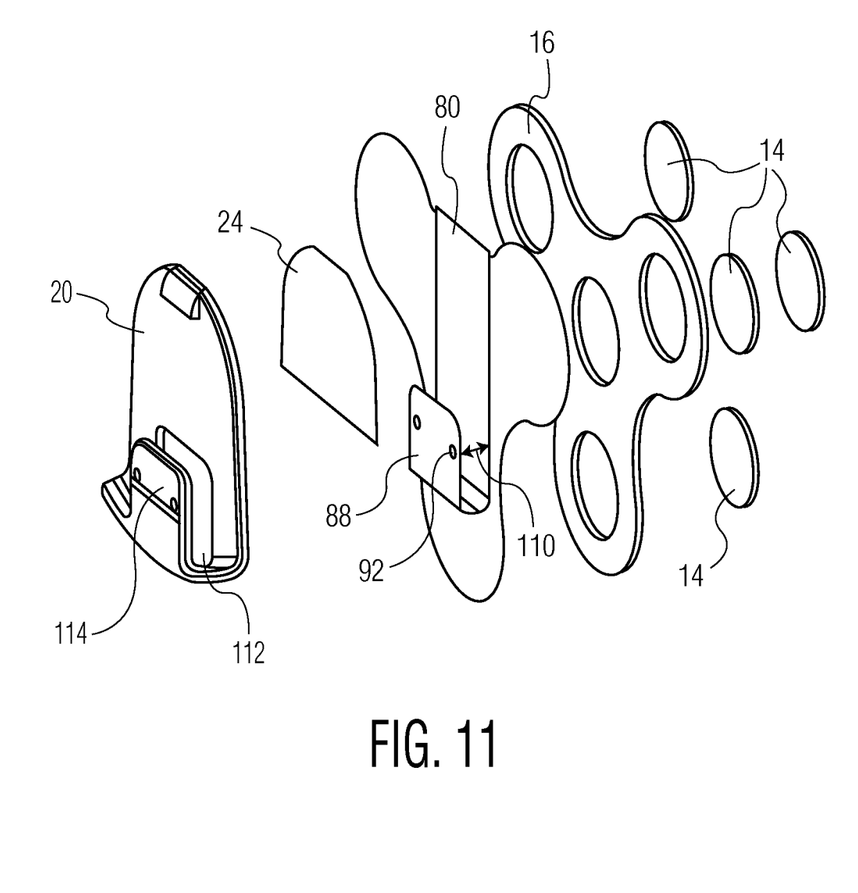
FIG. 11 is an exploded view of an assembly including the electrode patch of FIG. 9.

Referring to FIG. 11, the tab portion 80 may be folded as illustrated such that the terminal portion 88 is doubled back over the tab portion 80 and is positioned a distance 110 above the tab portion 80. The adhesive layer 24 adhering the holster 20 to the film layer 28 may extend over the tab portion 80 and secure to the shield 30, or a dielectric layer formed over the shield 30 on either side of the tab portion 80. The holster 20 may include an aperture 112 through which the tab portion 80 extends. A projection 114 extends over the aperture 112 and is secured to the terminal portion. Pins may extend downwardly from the projection 114 and into the alignment holes 92 in the terminal portion 88 and stiffener 90.

Figure 12:
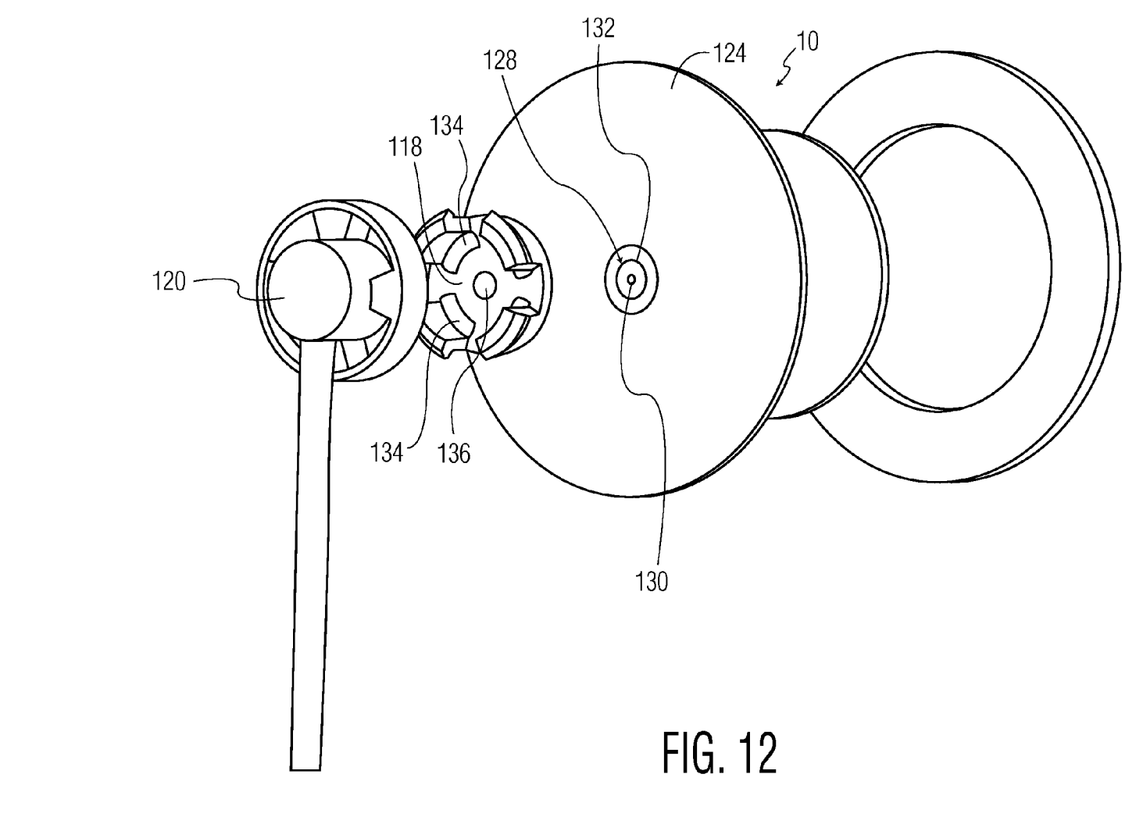
FIG. 12 is an exploded view of another alternative embodiment of an electrode patch in accordance with an embodiment of the present invention.
Figure 13:
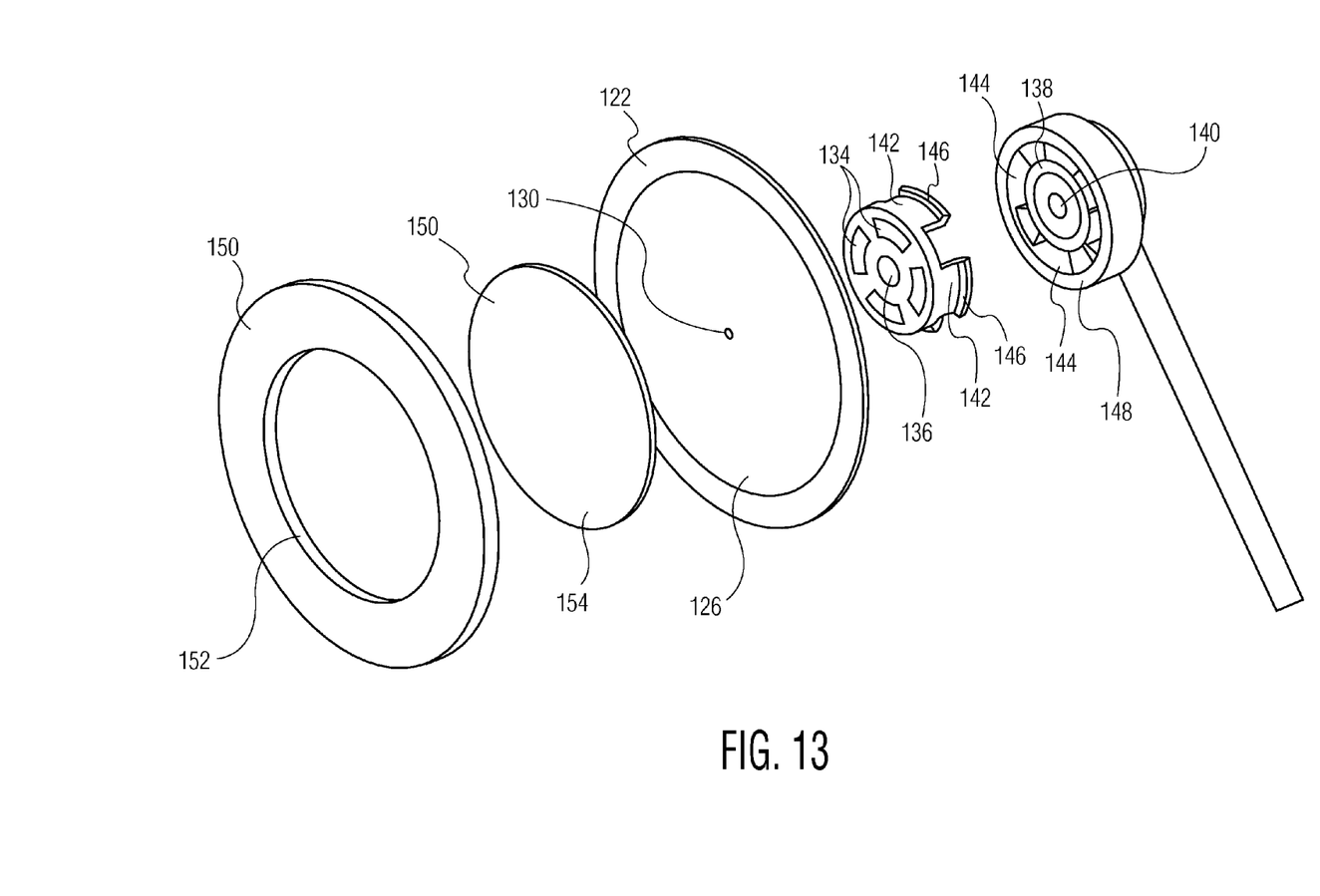
FIG. 13 is an exploded view of the electrode patch of FIG. 12 viewed from the opposite direction.
Figure 14:
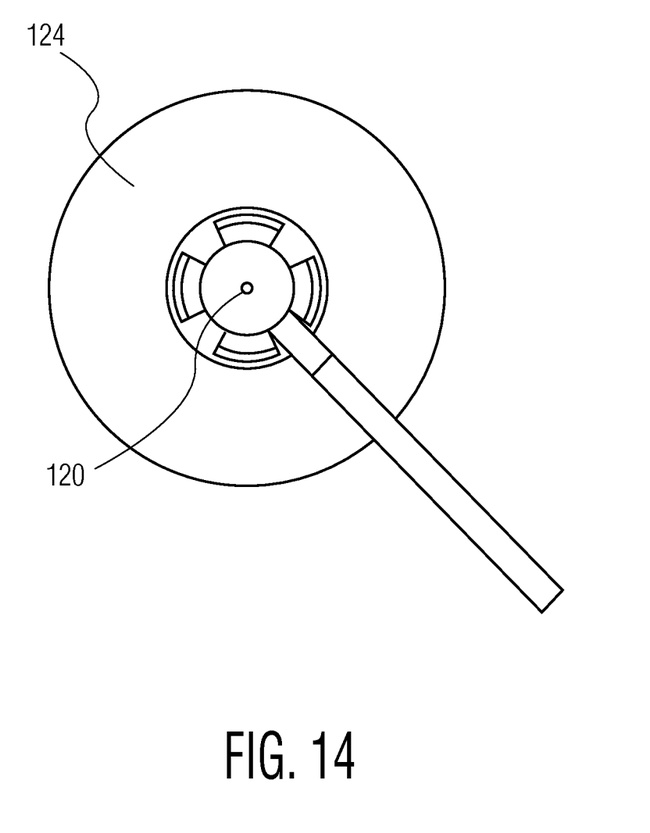
FIG. 14 is a top plan view of the electrode patch of FIG. 12.

Referring to FIGS. 12, 13, and 14, in an alternative embodiment, a patch 10 includes a receptacle 118 that receives a plug 120, or other connector in order to electrically couple the patch 10 to a monitoring apparatus, or other device. The receptacle 118 is secured to a film layer 122 having a shield 124 printed on an upper surface thereof and a contact pad 126 printed on a lower surface. A via 128 extends through the film layer and is electrically coupled to the contact pad 126. In the illustrated embodiment, the via 128 is conductive ink printed on either side of an aperture 130 extending through the film layer such that a conductive path is created. An unprinted region 132 may be formed around the via 128 such that the shield 124 is not electrically coupled to the via 128.

The receptacle 118 includes one or more receptacle shield contacts 134 and at least one receptacle via contact 136. In the illustrated embodiment, the shield contacts are located concentrically around the pad contact 136. The contacts 134, 136 may be formed of a conductive adhesive polymer and may extend through the receptacle 118. In use, the receptacle is secured to the shield 124 and via 128 by means of the adhesive contacts 134, 136. The connector 120 includes a connector shield contact 138 and a connector via contact 140 in positions corresponding to the contacts 134, 136 such that the contacts 138 electrically coupled to the contacts 134 and the contacts 140 electrically coupled to the contacts 136 when the connector 120 is positioned within the receptacle 118. The receptacle 118 may include one or more locking tabs 142 engaging apertures 144 formed on the connector 120. The locking tabs 142 may include hooks 146 engaging a rim 148 surrounding the apertures 144.

As with other embodiments of the patch 10, a foam layer 150 may secure to the lower surface of the film layer 122. The surface of the foam layer adjacent the film layer 122 may bear an adhesive such as MacTac MP597. The foam layer 150 may include an aperture 152 that receives an electrode 154 formed of a material such as hydrogel. A retaining layer and backing layer may also secure to patch 10 as in other embodiments described herein.

Figure 15:
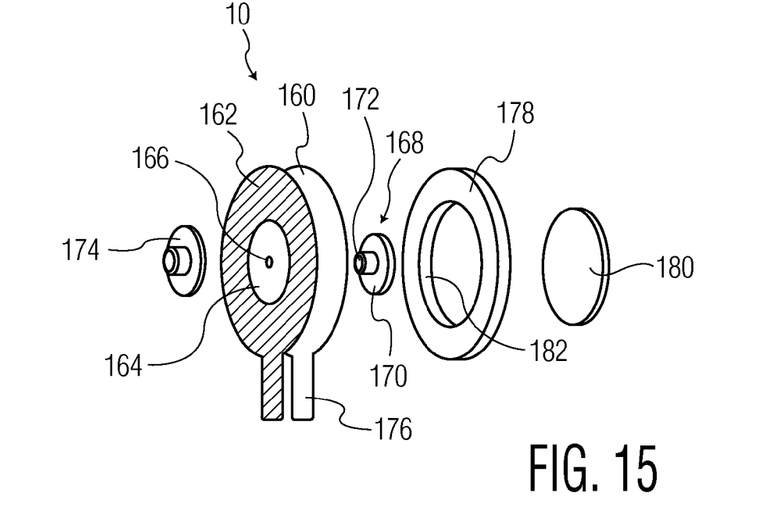
FIG. 15 is an exploded view of another alternative embodiment of an electrode patch in accordance with an embodiment of the present invention.
Figure 16:
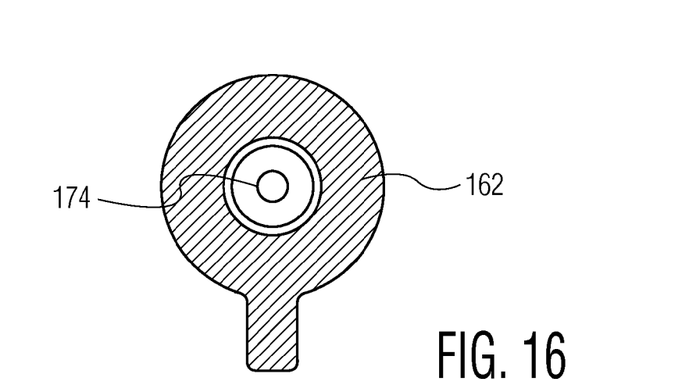
FIG. 16 is a top plan view of the electrode patch of FIG. 15.
Figure 17:
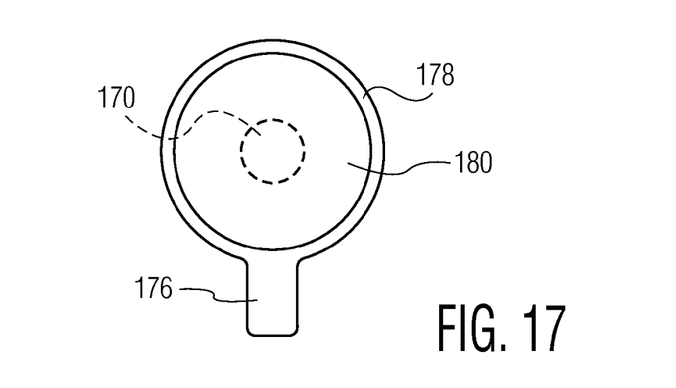
FIG. 17 is a bottom plan view of the electrode patch of FIG. 15.

Referring to FIGS. 15 through 17, in an alternative embodiment the biomedical electrode patch 10 includes a film layer 160 having a shield portion 162 printed or laminated on an upper surface thereof. In the illustrated embodiment, the shield portion 162 has an annular shaped portion surrounding a dielectric portion 164 printed or laminated on the film layer. An aperture 166 extends through the dielectric portion 164 and the film layer 160. A fastener 168 secures within the aperture 166. In the illustrated embodiment, the fastener 168 includes an eyelet 170 having a post 172 and a cap 174 sized to receive the post 172. The fastener 168 may be formed of a conductive plastic or may be bear a conductive coating or a conductive ink such as silver/silver chloride ink. The film layer 160 may include a tab portion 176 extending outwardly therefrom. The shield portion 162 may extend over the tab portion 176. In some embodiments, a connector secures to the tab portion 176 in order to electrically couple the shield portion 162 to a monitoring device.

A foam layer 178 may secure to the lower surface of the film layer 160 and a conductive interface 180 may be positioned within an aperture 182 in the foam layer in electrical contact with the fastener 168. In the illustrated embodiment, the conductive interface 180 is formed of hydrogel and may have a thickness slightly greater than that of the foam layer 178 such that it projects slightly.

Figure 18:
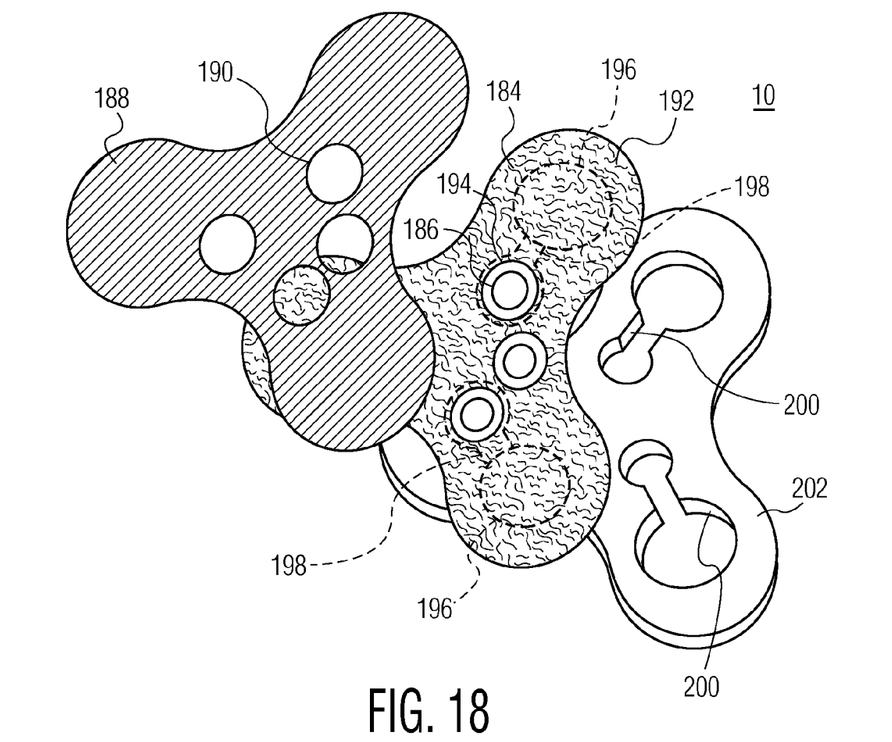
FIG. 18 is an exploded view of another alternative embodiment of a shielded electrode patch in accordance with an embodiment of the present invention.

Referring to FIG. 18, in an alternative embodiment, a biomedical electrode patch 10 includes a film layer 184 having a number of apertures 186 formed therein. A shield layer 188 formed of a conductive material is printed or laminated onto the film layer 184. The shield layer 188 includes apertures 190 corresponding in position to the apertures 186. The apertures 190 in the shield layer 188 may be slightly larger than the apertures 186. In the illustrated embodiment, a dielectric layer 192 is positioned between the shield layer 188 and the film layer 184. The dielectric layer 192 may include apertures 194 corresponding in position to the apertures 186 and being slightly larger than the apertures 186. The dielectric layer 192 may advantageously reduce the capacitance between the shield layer 188 and electrodes 196 positioned below the film layer 184 for contacting a patient's skin.

Traces 198 may extend from the electrodes 196 across the apertures 186 such that a connector may secure to the patch 10 and electrically contact the electrodes 194. The traces 198 and electrodes 196 may be formed of hydrogel. Each trace 198 may be monolithically formed with one of the electrodes 196. The electrodes 196 and traces 198 may fit within apertures 200 within a foam layer 202 secured to the lower surface of the film layer 184.

Figure 19:
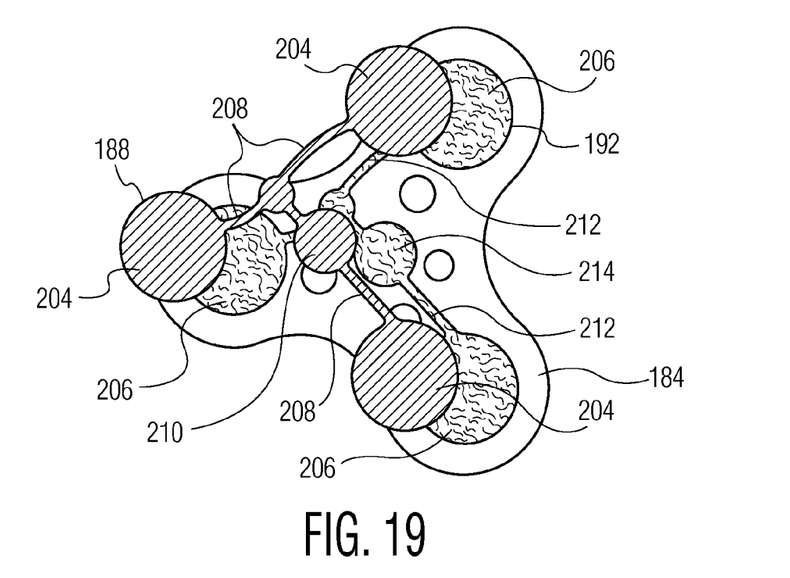
FIG. 19 is an exploded view of another alternative embodiment of an electrode patch in accordance with an embodiment of the present invention.

Referring to FIG. 19, in an alternative embodiment of the biomedical electrode patch of FIG. 18, the shield layer 188 includes portions 204 corresponding in size and position to the electrodes 196 and covering the electrodes and traces on the opposite side of the printed film circuit layer. The dielectric layer 192 may likewise include dielectric portions 206 corresponding in size and position to the electrodes 196. The electrode-covering portions 204 of the shield layer 186 may be connected to one another by traces 208. In some embodiments, a contact pad 210 is connected to the traces 208. The contact pad 210 may electrically contact a connector which also electrically contacts the electrodes 196. The dielectric layer 192 may overlap the printed conductive trace portions 212 on the film layer 184. The embodiment of FIG. 19 may advantageously be more flexible than the embodiment of FIG. 18 inasmuch as portions of the shield layer 188 and dielectric layer 196 have been removed.

What is claimed is:

1. A biomedical electrode comprising:
a film layer having an upper surface and a lower surface, the upper surface bearing a conductive layer having a shield portion, a dielectric layer, and at least one contact portion comprising a conductive material, the at least one contact portion extending through the dielectric layer and the film layer; and
an electrode layer configured to conduct electrical signals from a patient's skin, the electrode layer adjacent the lower surface and contacting the contact portion through the film layer,
wherein the shield portion has an annular shaped portion which substantially surrounds the contact portion and the dielectric layer and covers the electrode layer carried by the film layer.

2. The electrode of claim 1, further comprising a compressible layer attached to the lower surface, the compressible layer having an aperture formed therein to receive an electrically conductive skin-contacting hydrogel layer which contacts the electrode layer.

3. The electrode of claim 2, wherein the compressible layer has an undeformed thickness less than the thickness of the hydrogel layer.

4. The electrode of claim 1, wherein the electrode layer further comprises a skin-contacting hydrogel.

5. The biomedical electrode of claim 1, wherein the film layer further comprises a tab portion, and further wherein the shield portion extends over the tab portion.

6. The biomedical electrode of claim 5, wherein the tab portion and the shield portion are disposed to couple to a connector in order to electrically couple the shield portion to a monitoring device.

7. A biomedical electrode patch for connecting to a monitoring device comprising:
a substrate having upper and lower surfaces and a tab portion;
a dielectric layer disposed on the upper surface;
a conductive layer formed on the upper surface and having a shield portion surrounding the dielectric layer and extending over the tab portion;
a fastener extending through the substrate and the dielectric layer; and
an electrode configured to conduct electrical signals from a patient, the electrode adjacent the lower surface of the substrate in electrical contact with the fastener;
wherein the tab portion is disposed to couple to a connector in order to electrically couple the shield portion to the monitoring device.

* * * * *